United States Patent [19]
Müller-Berghaus et al.

[11] Patent Number: 5,610,024
[45] Date of Patent: Mar. 11, 1997

[54] METHOD FOR THE DETERMINATION OF LUPUS ANTICOAGULANT ANTIBODIES THAT CAUSE THROMBOSIS

[75] Inventors: Gert Müller-Berghaus; Bernd Pötzsch, both of Giessen; Christoph Seelig, Asslar, all of Germany

[73] Assignee: Max-Planck-Gesellschaft zur Förderung der Wissenschaften e.V., Gottingen, Germany

[21] Appl. No.: 412,854

[22] Filed: Mar. 29, 1995

Related U.S. Application Data

[63] Continuation of Ser. No. 116,685, Sep. 7, 1993, abandoned.

[30] Foreign Application Priority Data

Sep. 8, 1992 [DE] Germany ............................ 42 29 933.0

[51] Int. Cl.⁶ ............................................ C12Q 1/56
[52] U.S. Cl. .................... 435/13; 435/6; 435/7.1; 435/7.21; 435/7.4; 436/69; 436/501; 436/506; 436/548
[58] Field of Search ................................ 435/6, 7.1, 7.21, 435/13, 7.4; 436/501, 506, 35, 69, 63, 548, 811

[56] References Cited

U.S. PATENT DOCUMENTS

| | | | |
|---|---|---|---|
| 4,908,314 | 3/1990 | Orthner | 435/219 |
| 4,959,318 | 9/1990 | Foster et al. | 435/69.1 |
| 5,472,852 | 12/1995 | Smirnov et al. | 435/13 |

FOREIGN PATENT DOCUMENTS

| | | |
|---|---|---|
| WO91/02812 | 3/1991 | WIPO. |
| WO92/10586 | 6/1992 | WIPO. |
| 9310261 | 5/1993 | WIPO. |

OTHER PUBLICATIONS

Derwent Publications Ltd., London, GB; Class B04, AN 93-267048; "In-vitro lupus anticoagulant determin. comprises adding phospholipid, calcium ion and protein C-type activating substance in sample blood sample and determining coagulation time" & JP-A-5 180 835 (SRL KK) 23 Jul. 1993.

Exner, Thomas, "Similar Mechanism of Various Lupus Anticoagulants", *Thrombosis and Haemostasis*, No. 1, vol. 53: 15–18 (Feb. 18, 1985).

R. Bick et al, "The Antiphospholipid and Thrombosis (APL–T) Syndromes", Clinics In Laboratory Medicine, 15(1):63–84, Mar. 1995.

M. Bokarewa et al, "A new variant of interaction between phospholipid antibodies and the protein C system", Blood Coag. and Fibrin. 5(1):37–41, Feb. 1994.

R. Cariou et al, "Inhibition of Ptotein C Activation by Endothelial Cells in the Presence of Lupus Anticoagulant", N. Eng. J. of Med., 314(18):1193–1194, May 1986.

T. Exner, "Some recent developments with lupus anticoagulants", Blood Coag. and Fibrin. 5(2):281–289, Apr. 1994.

R. Malia et al, "Inhibition of activated protein C and its cofactor protein S by antiphospholipid antibodies", Br. J. of Haemat. 76:101–107, 1990.

E. Marciniak et al, "Impaired Catalytic Function of Activated Protein C: A New In Vitro Manifestation of Lupus Anticoagulant", Blood., 74(7):2426–2432, Nov. 1989.

T. Nakase et al, "Increased activated protein C–protein C inhibitor complex level in patients positive for lupus anticoagulant," Blood Coag. and Fibrin. 5(2):173–177, Apr. 1994.

J. Rauch et al, "Distinguishing Plasma Lupus Anticoagulants from Anti–Factor Antibodies Using Hexagonal (II) Phase Phospholipids," Thromb. Haemo. 62(3):892–896, Nov. 1989.

A. Sonnenwirth et al (eds)., "Gradwohl's Clinical Laboratory Methods And Diagnosis", vol. One, 8th edition (C.V. Mosby Company 1980), pp. 1020–1033.

Brandt, Thrombosis & Haemostasis (1991) 66:453–458.

Tsakiris, D. A. et al, J. Rheumatology (1990) 17:785–789.

*Primary Examiner*—Carol A. Spiegel
*Attorney, Agent, or Firm*—Nikaido, Marmelstein, Murray & Oram LLP

[57] ABSTRACT

In order to determine lupus anticoagulant (LA) antibodies in blood, plasma or tissue samples by means of the inhibitory effect of these antibodies on the neutralizing effect of protein C on the blood coagulation system, a defined amount of activated protein C is added to the sample, after incubation the remaining amount of a physiological substrate of protein C or protein S activity in the sample is determined according to known methods and the amount of LA antibodies present is calculated by comparison with a standard containing no LA antibodies. The method according to the present invention can be used to diagnose a predisposition to thrombotic events or disease-dependent risk of thrombosis as well as to monitor a therapy.

13 Claims, 2 Drawing Sheets

METHOD FOR THE DETERMINATION OF LUPUS ANTICOAGULANT ANTIBODIES THAT CAUSE THROMBOSIS

This application is a continuation of application Ser. No. 08/116,685, filed Sep. 7, 1993, now abandoned.

DESCRIPTION

The invention concerns a method for the determination of LA antibodies (lupus anticoagulant) in blood, plasma, plasma fractions and tissue extracts by their influence on the phospholipid-dependent anticoagulant activity (anticoagulant activity, anticoagulatory activity) of activated protein C (APC). The method according to the present invention can be used to diagnose certain predispositions or diseases, to monitor the course of a disease or to monitor a therapy.

Antiphospholipid antibodies (aPL) are autoantibodies which occur in persons in association with arterial and/or venous occlusions, thrombocytopenia and/or stontaneous abortions (reference: Lechner, K., Pabinger-Fasching, I., Haemostasis 15 (1985), 254–262; Branch, D. W. et al., N. Engl. J. Med. 313 (1985), 1322–1326; Exner, T., Thromb. Haemostas. 53 (1985), 15–18). aPLs can be detected by various tests e.g. by an ELISA using various phospholipids as the antigen or by conventional flocculation tests. Those aPLs which can be detected by coagulation tests are denoted LA antibodies (lupus anticoagulant). LA antibodies interfere with the phospholipid-dependent clotting steps and therefore prolong the coagulation times of various tests without inhibiting the activity of individual coagulation factors. But they do not represent a uniform group of autoantibodies against a sufficiently defined antigen. Malia et al., British Journal of Haematology 76 (1990), 101–107, mention a possible connection between antiphospholipid antibodies and thrombotic risk. The investigations which led to this finding were carried out on IgG fractions isolated from patient plasma with addition of purified activated protein C as well as of protein S and phosphatidylserine and phosphatidylcholine. This led to the conclusion that antiphospholipid antibodies have an inhibitory effect on complexes of activated protein C and protein S.

However, it is not possible using the tests available up to now to predict with sufficient certainty and rapidity for clinical application if a patient with detected aPL really also has a thrombotic risk (reviews: Triplett, D. A., Sem. Thromb. Hemostas. 16 (1990), 182–192; Jouhikainen, T. et al., Blood Coagul. Fibrinol. 3 (1992) 407–414).

Several methods are known for the determination of LA antibodies:

a. Determination of recalcification time (review: Rosner, E. et al., Thromb. Haemostas. 57 (1987), 144–147). This method has a low sensitivity and specificity.

b. Determination of the activated partial thromboplastin time using different activators and phospholipids (review: Hemostasis Committee of the "Societe Francaise de Biologie Clinique", Thromb. Res. 66 (1992), 349–364). The sensitivity and specificity of this test are very low.

c. Determination of the kaolin coagulation time or kaolin coagulation time index (KCT) (review: Exner (1985) supra). These tests have proven to be relatively good at detecting a lupus anticoagulant. There is no correlation between the occurrence of a thrombosis and positive detection of the lupus anticoagulant which this test is to determine.

d. Determinations by means of Dilute Russell's Viper Venom Time (reviews: Hemostasis Committee of the Societe Francaise de Biologie Clinique (1992) supra; Jouhikainen et al. (1992) supra). A lupus anticoagulant can be determined with a relatively high sensitivity using this test, however, there is no correlation between a positive test result and a risk of thrombosis.

e. Thrombocyte-neutralization test (reviews: Hemostasis Committee of the Societe Francaise de Biologie Clinique (1992) supra; Lazarchick, J. et al., Arch. Pathol. Lab. Med. 113 (1989), 177–180). Only autoantibodies whose anticoagulant activity can be neutralized in vitro by thrombocytic phospholipids can be detected by this test. There is no correlation between a positive test for lupus anticoagulant and risk of thrombosis.

The above-mentioned methods are more or less imprecise and above all have the disadvantage that they only determine certain functions of the LA antibodies but do not give any information regarding the risk of thrombosis. This negative correlation between the detection of LA antibodies and risk of thrombosis is explained by the fact that the in vivo effect of LA antibodies is not known. An impairment of fibrinolytic activity (Tsakiris et al., Thromb. Haemostas. 61 (1989), 175–177; Nilsson, T. K., Löfvenberg, E., Clin. Rheumatol. 8 (1989), 58–63), delayed formation and release of prostacyclin (Schorer et al., Br. J. Haematol. 71 (1989), 399–407), increased release of Willebrand factor (Byron et al., Ann. Rheum. Dis. 46 (1987), 741–745) and impaired activation of protein C (Tsakiris et al., J. Rheumatol. 17 (1990), 785–789) have been reported as possible explanations. A common feature of all these possible explanations is the primary binding of LA antibodies to the endothelial cell surface which leads to an impaired endothelial function. However, extensive investigations have shown that these pathophysiological explanations listed above apply to some but not the majority of patients with LA antibodies.

The object of the present invention is therefore to develop a method for the specific and quantitative determination of LA antibodies that cause thrombosis. It should be possible to carry out the test simply and rapidly and above all the test should have a high specificity with regard to the risk of thrombosis.

The object is achieved according to the present invention by a method for the determination of lupus anticoagulant (LA) antibodies in blood, plasma or tissue samples by means of the inhibitory effect of these antibodies on the neutralizing effect of protein C on the blood coagulation system in which a defined amount of activated protein C is added to the sample, after incubation the remaining amount of a physiological substrate of protein C or the protein S activity in the sample is determined according to known methods and the amount of LA antibodies present is calculated by comparison with a standard containing no LA antibodies. This method is based on the known reaction of phospholipid-dependent proteolytic cleavage in particular of factor VIIIa or factor Va by activated protein C. In order to circumvent the problem of differing concentrations of protein C in various test samples, activated protein C is added to the test sample and the inhibition (neutralization) of the anticoagulatory activity of activated protein C towards physiological substrates is determined in the presence of anti-phospholipid antibodies. The rate of inhibition (neutralization) of activated protein C activity does not correlate with the concentration of measured LA antibodies in a group of patients with detected LA antibodies. However, using the test according to the present invention it is possible to show that the rate of inhibition of protein C activity correlates very well with the incidence of thrombotic events.

Any physiological substrate of activated protein C, i.e. in particular factor VIIIa and factor Va, can be used as the substrate for activated protein C within the scope of the present invention. The effect of LA antibodies can also be determined by means of a system for the determination of protein S activity. Coagulation tests, preferably using chromogenic substrates and also monospecific antibodies are particularly suitable for the detection of the proteolytic action of activated protein C on factors VIIIa and Va.

In this test it is especially preferred to detect the activity of activated protein C via proteolysis of activated factor VIIIa although this is not essential for the present invention and it is only important to determine the inhibition of the phospholipid-dependent reaction between activated protein, protein S and physiological substrate. Thus within the scope of the method according to the present invention the inhibition of the enzymatic action of activated protein C is determined depending on LA antibodies.

Within the scope of the method according to the present invention it it preferable to use purified protein C, in particular protein C produced by recombinant means.

Within the scope of the method according to the present invention protein C is preferably activated by thrombin or snake venom, and in particular by thrombin or snake venom coupled to a solid phase. Coupling to CNBr-activated SEPHAROSE 4B (cross-linked agarose) was in this case carried out according to the manufacturer's instructions: "Methods for coupling ligands to CNBr-activated Sepharose 4B" in Affinity Chromatography—principles and methods—Pharmacia LKB Biotechnology, Uppsala, Sweden, information brochure.

It may be necessary to pretreat the samples in order to determine LA antibodies causing thrombosis in plasma fractions, cell extracts or in punctuates with a low activity of a substrate for activated protein C. In this process a physiological substrate for protein C, in particular factor VIIIa or factor Va, is added to the patient plasma.

In this process it is particularly preferable to add a labelled substrate, especially factor Va and factor VIIIa, in particular a substrate labelled with a dye, e.g. fluorescent dye.

It can also be advantageous to also add protein S in addition to activated protein C to the sample to ensure an adequate formation of complex between protein C and proteins.

In a particularly preferred embodiment the plasma to be tested is incubated with activated protein C and subsequently, depending on the substrate to be determined, a corresponding deficient plasma, i.e. factor VIII-deficient or factor V-deficient plasma, is added in order to determine the remaining factor VIIIa activity in a coagulation test.

The present invention enables a determination of the neutralizing activity of the anticoagulatory activity of APC to be carried out simply and rapidly which can be advantageously used for diagnosis and therapy of diseases. The occurrence of these diseases is associated with the formation of LA antibodies which in turn is a further object of the present invention as a method for diagnosing a predisposition to thrombotic events or of disease-dependent risk of thrombosis as well as for monitoring therapy. The method according to the present invention enables the determination of LA antibodies without isolating the antibodies from plasma. The determination can be carried out directly in the blood, plasma or punctate of the patient and is correspondingly quick and cheap compared to other test methods.

Furthermore the present invention also concerns a reagent, which is suitable for the determination of LA antibodies that cause thrombosis, which contains protein C together with the components of a coagulation test and preferably of a factor VIIIa activity test.

The following examples elucidate the invention further in conjunction with the attached figures. These show:

EXAMPLE 1

Determination of APC-induced factor VIII inactivation in normal plasma

A) Production of activated protein C as a standardized enzyme in the reagent

Thrombin coupled to SEPHAROSE (cross-linked agarose) is incubated with purified protein C for one hour at 37° C. The ratio of thrombin to protein C is 1:30 (mol/mol). The amount of activated protein C (APC) which formed is determined in a protein C activity test in order to ensure that the amount of protein C used has been completely inactivated. A protein C activity test using a chromogenic substrate has proven successful. APC can be stored lyophilised until use in the test.

B) Test procedure

1. Two-step test

50 µl sample solution are added to 200 µl APC so that a final concentration of APC between 0.1 and 1.5 µM is achieved in the mixture. APC and sample solution are mixed and incubated for 2 minutes at 37° C. 100 µl of the mixture are subsequently mixed with 100 µl factor VIIIa-deficient plasma and 100 µl of a reagent to determine the partial thromboplastin time. After incubating again as instructed for the determination of factor VIIIa activity, it is started by addition of 100 µl calcium chloride (25 mM). The time period from the start of addition of the calcium chloride solution until formation of a clot is registered visually or using an automated system.

2. Single-step test

20 µl sample solution is added to 80 µl APC so that a final concentration between 0.01 and 1.5 µM is achieved in the mixture of APC and sample. APC and sample solution are mixed and incubated for 2 minutes at 37° C. Subsequently 100 µl factor VIII-deficient plasma and 100 µl of a reagent for the determination of partial thromboplastin time are added to the reaction mixture and mixed. After incubating again as instructed for the determination of the factor VIII activity, it is started by addition of 100 µl calcium chloride (25 mM). The time period from the start of addition of the calcium chloride solution until formation of a clot is registered visually or using an automated system.

EXAMPLE 2

Figure 1:
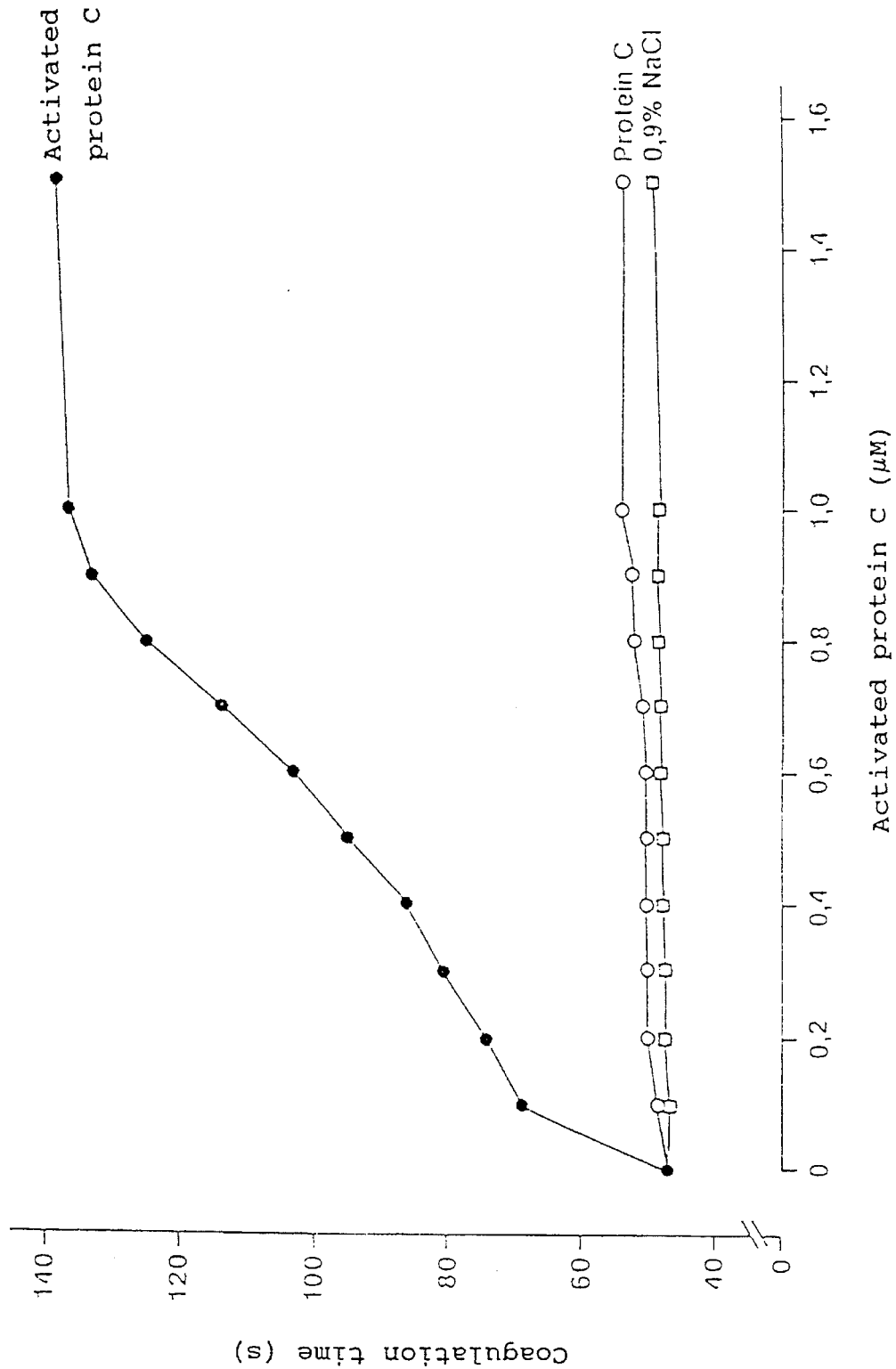
FIG. 1: A graphic representation of the coagulation times of a factor VIII activity test plotted against the concentration of activated protein C.
Figure 2:
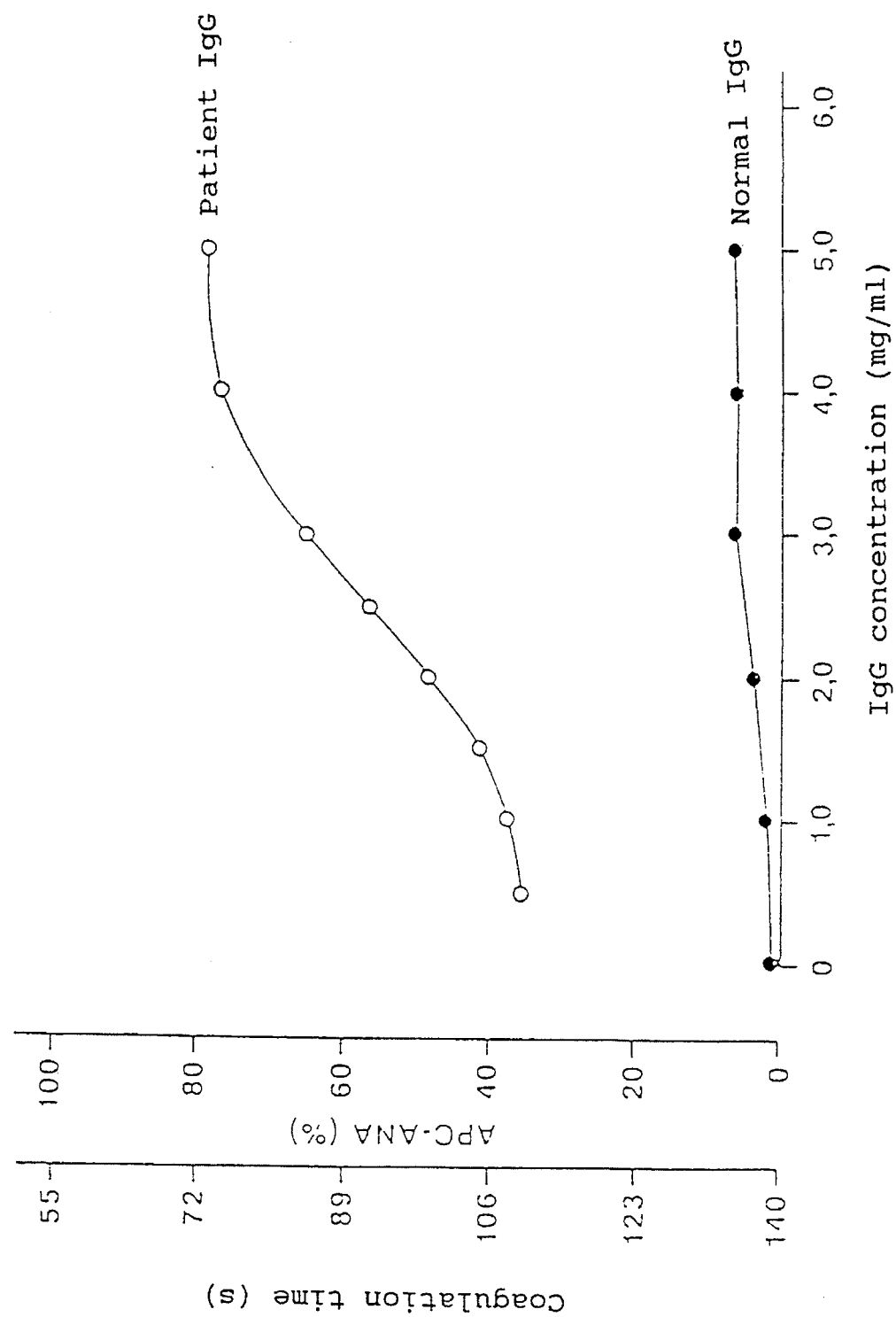
FIG. 2: A graphic representation of the APC anticoagulant-neutralization activity (APC-ANA) of immunoglobulins isolated from the plasma of a patient compared to normal immunoglobulin. The coagulation times and the corresponding APC-ANA values are shown. The neutralizing activity determined according to the method described in example 1 is plotted in relation to the immunoglobulin concentration.

Determination of the APC anticoagulant neutralizing activity (APC-ANA) of immunoglobulins isolated from human patient plasma. In order to show the specificity of the test the immunoglobulin fraction was isolated from patient plasma and the effect of the immunoglobulins in the test described above was determined in a dose-effect curve. Immunoglobulins from patient plasma and normal immunoglobulins were incubated with APC for 5 minutes at 37° C. Subsequently factor VIII-deficient plasma, and reagent for determining the partial thromboplastin time were added and after a further incubation period calcium chloride was added. FIG. 2 shows that there is an increased inhibition (neutralization) of the APC anticoagulatory activity with increasing IgG concentration of patient IgG. Zero % neutralizing activity represents maximum proteolysis of activated factor VIIIa. Coagulation times of about 140 s are measured in the test (see FIG. 1). One hundred per cent neutralizing activity represents 100% neutralization of the APC anticoagulatory activity corresponds to a coagulation time when non-activated protein C or physiological saline is used instead of activated protein C in the test mixture. (FIG. 1).

EXAMPLE 3

Determination of the APC anticoagulant neutralizing activity (APC-ANA) in human plasma samples. A pool plasma or the patient plasma is used as the sample solution in the test mixture as described in example 1 in order to determine the neutralizing activity in normal plasma (pooled plasma of about 20 healthy blood donors) and in the patient plasma. A coagulation time of about 140 s is measured as the test result for normal pool plasma when using activated protein C at a concentration of 1 μM (FIG. 1 and Table 1). When patient plasma is used instead of normal plasma the coagulation time is reduced to about 70 s (Table 1). If the same patient plasma is incubated with non-activated protein C, a coagulation time is determined which is identical to the value after incubating patient plasma with physiological saline (Table 1). The coagulation time may be slightly longer than with normal plasma since LA antibodies do not only show APC-neutralizing activity but also react with further steps in the coagulation test. For this reason the difference between the value obtained when incubating patient plasma with APC and the value after incubation of patient plasma with non-activated protein C is selected for the determination of the APC anticoagulant neutralizing activity (Table 1).

TABLE 1

Coagulation times in the factor VIII activity test after incubation of normal plasma or plasma samples of two patients (patient 1, patient 2) with activated protein C (APC) or non-activated protein C (PC). The difference between these two values in seconds corresponds to the factor VIII inhibition in percent. 100% of the factor VIII inhibition in percent represents the APC anticoagulant neutralizing activity (APC-ANA).

|  | Coagulation time after incubation with | | Difference between coagulation times | Factor VIII inhibition | APC-ANA |
|---|---|---|---|---|---|
|  | APC (s) | PC (s) | (s) | (%) | (%) |
| Normal plasma | 141 | 55 | 86 | 100 | 0 |
| Patient 1 | 96 | 56 | 40 | 46 | 54 |
| Patient 2 | 87 | 54 | 33 | 38 | 62 |

We claim:

1. A method for determining the presence or amount of lupus anticoagulant (LA) antibodies in a sample of plasma or tissue, wherein said LA antibodies selectively inhibit activated protein C, said method consisting essentially of:

a) contacting said sample with said activated protein C, b) contacting said sample from step a) with reactants for determining factor VIIIa activity to form a reaction mixture, c) incubating said reaction mixture, d) determining any factor VIIIa activity in said reaction mixture, and e) comparing the factor VIIIa activity in said reaction mixture with factor VIIIa activity obtained by contacting a standard sample which does not contain any LA antibodies with said reactants, wherein any increase in factor VIIIa activity in said reaction mixture relative to the factor VIIIA activity obtained from said standard sample indicates the presence or amount of said LA antibodies which selectively inhibit said activated protein C in said sample.

2. Method according to claim 1, wherein said activated protein C is provided by addition of purified activated protein C.

3. Method according to claim 1, wherein said activated protein C is provided by addition or recombinant protein C.

4. Method according to claim 1, wherein said activated protein C is provided by in vivo activation of endogenous protein C by addition of thrombin or snake venom.

5. Method according to claim 4, wherein said added thrombin or snake venom is coupled to a solid phase.

6. Method according to claim 1, wherein said factor VIIIa activity is determined by a coagulation test which detects the factor VIIIa activity remaining in said reaction mixture after proteolysis of factors VIIIa and Va by said activated protein C.

7. Method according to claim 6, wherein chromogenic substrates or monospecific antibodies are used to determine said factor VIIIa activity remaining in said reaction mixture, in said coagulation test.

8. Method according to claim 1, wherein labelled factor VIIIa is added to the sample prior to step c).

9. Method according to claim 1, wherein said reactants for determining factor VIIIa activity comprise factor VIII deficient plasma.

10. Method according to claim 1, further comprising addition of a complex of activated protein C and protein S to the sample prior to step c).

11. Method according to claim 1, wherein said activated protein C is added to produce a final concentration of 0.1 to 1.5 μM in said reaction mixture.

12. The method according to claim 1, wherein said tissue sample is blood.

13. A method of screening a patient for a predisposition to thrombosis due to a disease in which LA antibodies which selectively inhibit activated protein C are present, comprising the following steps:

a) contacting said sample with said activated protein C, b) contacting said sample from step a) with reactants for determining factor VIIIa activity to form a reaction mixture, c) incubating said reaction mixture, d) determining any factor VIIIa activity in said reaction mixture, and e) comparing the factor VIIIa activity in said reaction mixture with factor VIIIa activity obtained by contacting a standard sample which does not contain any LA antibodies with said reactants, wherein any increase in factor VIIIa activity in said reaction mixture relative to the factor VIIIA activity obtained from said standard sample indicates said predisposition to thrombosis in said patient.

* * * * *